US00PP30272P3

(12) United States Plant Patent
Biancheri

(10) Patent No.: US PP30,272 P3
(45) Date of Patent: Mar. 5, 2019

(54) ***RANUNCULUS ASIATICUS* PLANT NAMED 'ABPERKONS'**

(50) Latin Name: *Ranunculus asiaticus*
Varietal Denomination: ABPERKONS

(71) Applicant: Alberto Biancheri, Camporosso Mare (IT)

(72) Inventor: Alberto Biancheri, Camporosso Mare (IT)

(73) Assignee: Impresa Individuale Biancheri Alberto (IT)

( * ) Notice: Subject to any disclaimer, the term of this patent is extended or adjusted under 35 U.S.C. 154(b) by 0 days.

(21) Appl. No.: 15/731,520

(22) Filed: Jun. 20, 2017

(65) Prior Publication Data

US 2018/0042162 P1 Feb. 8, 2018

(30) Foreign Application Priority Data

Aug. 5, 2016 (QZ) ..... PBR 2016/1920

(51) Int. Cl.
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
See application file for complete search history.

*Primary Examiner* — Anne Marie Grunberg
(74) *Attorney, Agent, or Firm* — Cassandra Bright

(57) ABSTRACT

A new and distinct *Ranunculus* cultivar plant named 'ABPERKONS' is disclosed, characterized by a unique flower color combination including soft pink and green-yellow. Plants are strong and produce an excellent quantity of flowering stems with large size flowers throughout the flowering season. The new variety is a *Ranunculus*, normally produced as a cut flower and potentially useful as an ornamental plant.

2 Drawing Sheets

Figure 1:
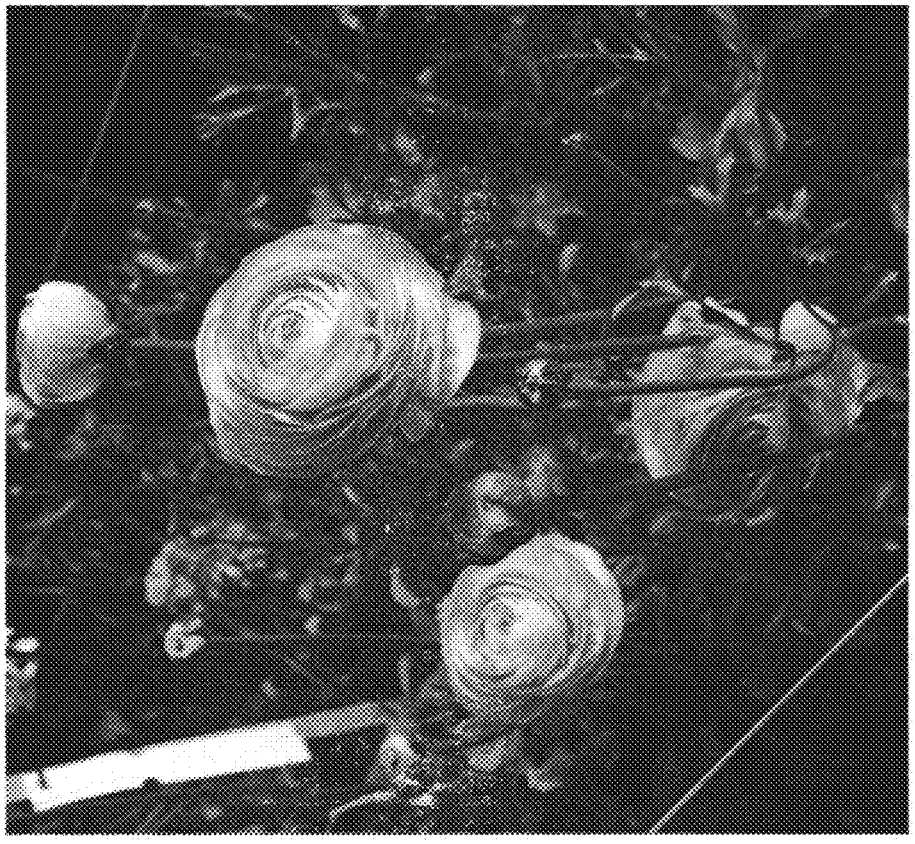

Latin name of the genus and species: *Ranunculus asiaticus*.

Variety denomination: 'ABPERKONS'.

BACKGROUND OF THE INVENTION

The new *Ranunculus* cultivar is a product of a planned breeding program conducted by the inventor, Alberto Biancheri in Camporosso Mare, Italy. The cross resulting in this new variety was made during 2005.

The seed parent is the, unpatented, proprietary variety referred to as *Ranunculus* 'SLE.1'. The pollen parent is the unpatented, proprietary variety referred to as *Ranunculus* 'SLE.2'. The new variety was discovered in 2009 by the inventor in a group of seedlings resulting from the 2005 crossing, in a research greenhouse in Camporosso Mare, Italy.

Asexual reproduction of the new cultivar was first performed by vegetative division of buds sprouting from the rhizome of the selected plant. Subsequent propagation has been performed by tissue culture. First propagation took place at a research greenhouse in Camporosso Mare, Italy in 2009 and has shown that the unique features of this cultivar are stable and reproduced true to type in multiple successive generations.

SUMMARY OF THE INVENTION

The cultivar 'ABPERKONS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ABPERKONS' These characteristics in combination distinguish 'ABPERKONS' as a new and distinct *Ranunculus* cultivar:

1. Unique soft pink and green-yellow flower color.
2. Large corolla typically produced over the entire harvest period.
3. Strong, vigorous plants.
4. Above average quantity of flower stems produced during the flowering season.

PARENT COMPARISON

Plants of the new cultivar 'ABPERKONS' are similar to plants of the seed parent, in most horticultural characteristics, however, plants of the new cultivar 'ABPERKONS' differ in the following;

1. The new variety has a different flower color. The new variety produces a flower which is light pink (near 62C) with a Green-Yellow center (near 1D), the seed parent has a single flower color of N57B.
2. Flower size of the new variety is larger. The new variety produces a larger flower, with an average diameter range of 9 to 12 cm, the seed parent has an average diameter range of 8 to 10 cm.

Plants of the new cultivar 'ABPERKONS' are similar to plants of the pollen parent, in most horticultural characteristics, however, plants of the new cultivar 'ABPERKONS' differ in the following;

1. The new variety has a different flower color. The new variety produces a flower which is light pink (near 62C)

with a Green-Yellow center (near 1D), the pollen parent has a single flower color of Yellow-Orange 19A.

2. Flowers of the new variety are double, flowers of the pollen parent are semi-double.
3. Flower size of the new variety is larger. The new variety produces a larger flower, with an average diameter range of 9 to 12 cm, the pollen parent has an average diameter range of 6 to 10 cm.

COMMERCIAL COMPARISON

Plants of the new cultivar 'ABPERKONS' are comparable to the unpatented commercial variety *Ranunculus* 'ABGNOWEE'. The two *Ranunculus* varieties are similar in most horticultural characteristics; however, the new variety 'ABPERKONS' differs in the following:

1. Flower color of the new variety is different.
2. The new variety produces a larger flower.
3. Floral stem length of the new variety is longer.

BRIEF DESCRIPTION OF THE PHOTOGRAPHS

The accompanying photograph in FIG. 1 illustrates in full color flowering plants of the new variety at approximately five months old, grown in a greenhouse.

Figure 2:
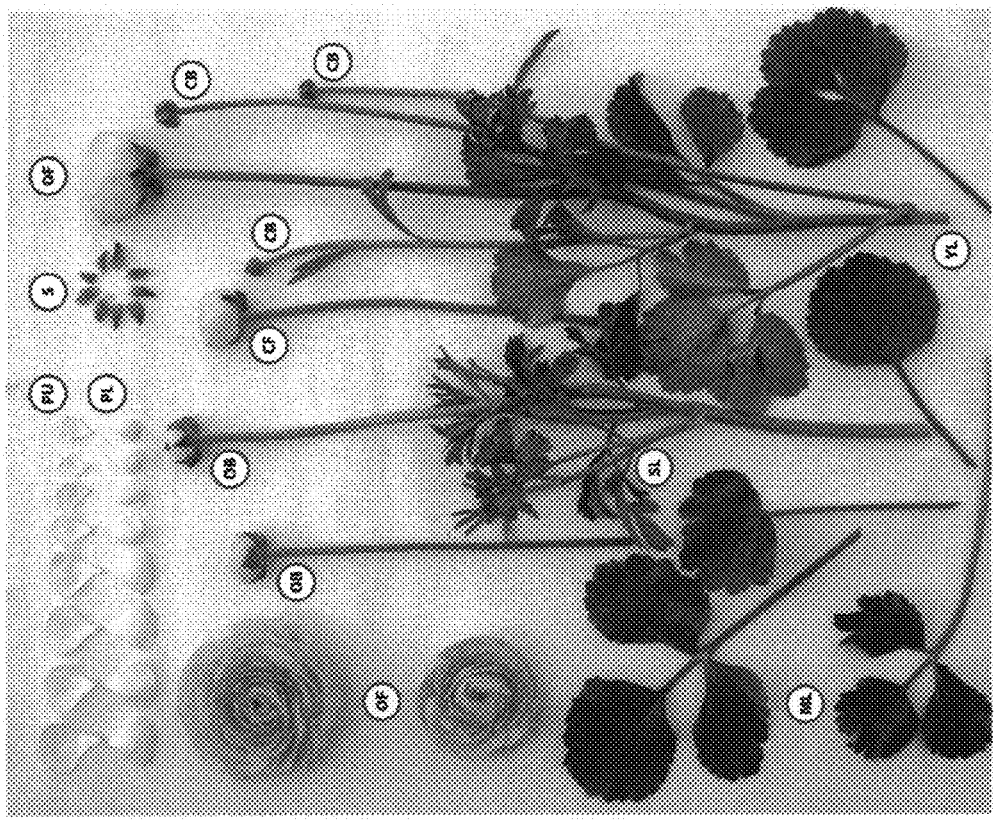

FIG. 2 illustrates a close up of plant parts.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 6$^{th}$ edition, except where general terms of ordinary dictionary significance are used. The following observations and measurements describe 'ABPERKONS' plants grown in a greenhouse Camporosso Mare, Italy. The plant described has been cultivated under glass, planted in the months of September and described in the month of February. One must always refer to these conditions of season and culture, when considering the present description. By reason of different climate or culture conditions, differences may arise between certain characteristics of the plant and the corresponding characteristics of the description. It should be considered as normal and do not modify the essence of the present invention because it will possible to identify the plant by means of the totality of the characteristics given in the description. The rhizome has been planted on raised benches in a peat and pumice substrate mixture. The growing temperature ranged from 12° C. to 25° C. during the day and from 2° C. to 8° C. during the night. General light conditions are bright, normal sunlight. Measurements and numerical values represent averages of typical plant types.

Botanical classification: *Ranunculus asiaticus* 'ABPERKONS'.

PROPAGATION

Time to rooting: 15 days at approximately 10-12° C.

Time to produce a rooted plantlet: 20 days.

Root description: Secondary roots grow from the rhizome and are fasciculate type.

PLANT

Growth habit: Herbaceous perennial, robust plant, erect vegetation.

Height to top flower: 60 to 65 cm.

Plant spread: 45 to 50 cm.

Growth rate: Medium.

Branching characteristics: Main floral stems grow from a basal rosette with 1 or 2 lateral branches, each one of which has 1 to 2 flowers.

Length of lateral branches: 55 to 60 cm.

Diameter of lateral branches: 0.4 to 0.8 cm.

Texture of lateral branches: Slightly tomentose.

Internode length: Internodes are extremely close together, forming a basal rosette.

Strength of lateral branches: Medium.

Color of lateral branches: Yellow Green (RHS 144A).

Angle of branches: 20° to 25°.

Number of leaves per lateral branch: Usually 2 or 4.

FOLIAGE

The leaves, usually numerous, have a marked heterophyllia, in relation to the degree of their development and their position on the plant (base of the plant; floral stem).

Leaf at the base of the plant:

- *Arrangement.*—Simple (young leaf, YL); Biternate (mature leaf, ML).
- *Average length.*—30 to 38 cm.
- *Average width.*—12 to 16 cm.
- *Overall shape of blade.*—Obovate (young leaf); Palmatipartite (mature leaf).
- *Dissected leaves, describe lobes, quantity of dissection.*—Young leaves are generally not lobed; mature leaves are generally divided in 3 parts, each one of which further divided in lobes.
- *Apex.*—Rounded.
- *Base.*—Rounded.
- *Attachment.*—Base of the plant.
- *Margin.*—Dentate.
- *Texture of top surface.*—Slightly tomentose, slightly verrucose.
- *Texture of bottom surface.*—Slightly tomentose.
- *Appearance of top surface.*—Matte.
- *Appearance bottom surface.*—Matte.
- *Leaf internode length.*—The internodes are extremely close together, forming a basal rosette.
- *Color.*—Young foliage upper side: Green (RHS 137B). Young foliage under side: Green (RHS 138B). Mature foliage upper side: Green (RHS 137B). Mature foliage under side: Green (RHS 138B).
- *Venation.*—Type: Dichotomous; plunging in to the limb at the upper surface; raised on the limb at the lower surface. Venation color upper side: Yellow Green (RHS 144A). Venation color under side: Yellow Green (RHS 144A).
- *Petiole.*—Petiole: Long, tubular, rigid. Length: 12 to 16 cm. Diameter: 0.3 to 0.6 cm. Pubescence: Slightly tomentose.
- *Color.*—Yellow Green (RHS 144A).

Leaf inserted at the nodes of the floral stems (sl):

- *Arrangement.*—Biternate.
- *Average length.*—15 to 25 cm.

*Average width.*—14 to 16 cm.
*Overall shape of blade.*—Palmatipartite.
*Dissected leaves, describe lobes, quantity of dissection.*—Generally simple or divided in 2 to 3 parts, each one of which is further divided in some lobes.
*Apex.*—Acute.
*Base.*—Acute.
*Attachment.*—Floral stems.
*Margin.*—Dentate.
*Texture of top surface.*—Slightly tomentose.
*Texture of bottom surface.*—Slightly tomentose.
*Appearance of top surface.*—Glossy.
*Appearance bottom surface.*—Glossy.
*Leaf internode length.*—5 to 10 cm.
*Color.*—Foliage upper side: Green (RHS 137B). Foliage under side: Green (RHS 138A).
*Venation.*—Type: Longitudinal, plunging in to the limb at the upper surface and raised on the limb at the lower surface. Venation color upper side: Yellow Green (RHS 144A). Venation color under side: Yellow Green (RHS 144A).
*Petiole.*—Petiole: Long, slightly flat, rigid. Length: 6.0 to 12.0 cm. Diameter: 0.3 to 0.6 cm. Pubescence: Slightly tomentose.
*Color.*—Yellow Green (RHS 144A).

FLOWER

Bloom period: Winter to Spring.
Vase life (cut flower): 10 to 15 days.
Persistent or self-cleaning: Self-Cleaning.
Bud:
*Closed bud (cb).*—Shape: Flattened globular with a sharp point. Length: 1.0 to 1.8 cm. Diameter: 1.1 to 1.2 cm. Color: Greyish Green (RHS NN137 A); Red-Purple (RHS 61A) along venations and near the base.
*Slightly open bud (ob).*—Shape: Flattened globular; the gynoecium is raised, clearly visible at the center of the corolla. Length: 1.6 to 2.0 cm. Diameter: 2.0 to 2.7 cm. Color: Red (RHS 36C) near margin; Yellow Green (RHS 145C).
Flower size (of):
*Diameter.*—9 to 12 cm.
*Height.*—3 to 4 cm.
Corolla (of): Round, regular, in the form of a flat section.
Petals:
*Arrangement.*—Imbricated, disposed on the receptacle in very tight verticils. The size of the petals is quite variable, according to the position in the corolla, decreasing from the exterior toward the center. The average size of fully developed petal is as follows: Lobe Length: 3.7 to 5.5 cm. Lobe Width: 3.0 to 5.2 cm.
*Quantity.*—Double flower, petals are very numerous (>100).
*Texture.*—Silky, thin, resistant.
*Lobe apex.*—Rounded.
*Lobe shape.*—Obovate.
*Margin.*—Entire.
*Aspect.*—Fan Shape, concave.
Color when opening (cf):
*Upper surface.*—Red Purple (RHS 61A) margin; Red (RHS 36C) fades to Yellow (RHS 1D) from margin to the base.
*Lower surface.*—Red Purple (RHS 61A) margin; Red (RHS 36C) fades to Yellow (RHS 1D) from margin to the base.
Color fully opened (of):
*Upper surface (pu).*—Red Purple (RHS 62C); Yellow (RHS 1D) near the base.
*Lower surface (pl).*—Red Purple (RHS 62C); Yellow (RHS 1D) near the base.
Calyx to sepals (s):
*Quantity per flower.*—6 to 9.
*Shape.*—Concave, Slightly incurved.
*Length.*—1.5 to 2.3 cm.
*Width.*—0.6 to 1.1 cm.
*Apex.*—Acute to Sub-obtuse.
*Base.*—Flat to Slightly rounded.
*Margin.*—Entire.
*Texture.*—Lower surface is tomentose; Upper surface is glabrous.
*Color upper surface.*—Green (RHS 138B).
*Color lower surface.*—Yellow Green (RHS 137C).
Peduncle: None.
Pedicel:
*Length.*—55 to 60 cm.
*Diameter.*—0.9 to 1.1 cm.
*Color.*—Yellow Green (RHS 144A).
*Orientation.*—Upright, straight, rigid.
*Pubescence.*—Slightly tomentose.
Fragrance: None.

REPRODUCTIVE ORGANS

Androecium:
*Stamens.*—Almost completely transformed as petals.
Gynoecium: The pistils are numerous, short, locked together at the center of the corolla in a Red Purple (RHS 59A), dome-shaped apocarpous gynoecium.

OTHER CHARACTERISTICS

Seeds and fruits: Seeds and fruit production not observed.
Disease and pest resistance: Neither resistance nor susceptibility to normal diseases and pests of *Ranunculus* has been observed.
Temperature tolerance: Upper and lower temperature tolerance not observed, plants have been grown in a climate controlled greenhouse. *Ranunculus asiaticus* typically tolerates temperatures within USDA Zones 7 to 11.

What is claimed is:

1. A new and distinct cultivar of *Ranunculus* plant named 'ABPERKONS' as herein illustrated and described.

* * * * *